(12) United States Patent
Ting

(10) Patent No.: US 10,515,189 B2
(45) Date of Patent: Dec. 24, 2019

(54) RADIO FREQUENCY MODULE AND RELATED MANAGEMENT SYSTEM

(71) Applicant: Wistron Corporation, New Taipei (TW)

(72) Inventor: Ssu-Han Ting, New Taipei (TW)

(73) Assignee: Wistron Corporation, New Taipei (TW)

( * ) Notice: Subject to any disclaimer, the term of this patent is extended or adjusted under 35 U.S.C. 154(b) by 1030 days.

(21) Appl. No.: 14/983,435

(22) Filed: Dec. 29, 2015

(65) Prior Publication Data
US 2016/0371461 A1 Dec. 22, 2016

(30) Foreign Application Priority Data
Jun. 18, 2015 (TW) .............................. 104119817 A

(51) Int. Cl.
*G06F 19/00* (2018.01)
(52) U.S. Cl.
CPC .................................. *G06F 19/3462* (2013.01)
(58) Field of Classification Search
CPC .................................................. G06F 19/3462
USPC ....................................................... 340/572.1
See application file for complete search history.

(56) References Cited

U.S. PATENT DOCUMENTS

| | | | | |
|---|---|---|---|---|
| 2006/0065713 A1* | 3/2006 | Kingery | .............. | G06F 19/3462 235/380 |
| 2012/0118977 A1* | 5/2012 | Gao | ................. | G06K 19/07771 235/492 |
| 2014/0260600 A1* | 9/2014 | Rike | .................... | G01F 23/2845 73/290 R |
| 2015/0033823 A1* | 2/2015 | Blumberg, Jr. | ........ | G01N 29/02 73/19.03 |
| 2015/0253174 A1* | 9/2015 | Barrett | .................. | G01F 23/263 73/304 C |

FOREIGN PATENT DOCUMENTS

| | | |
|---|---|---|
| CN | 101987216 A | 3/2011 |
| CN | 102622641 A | 8/2012 |
| CN | 102810721 A | 12/2012 |

OTHER PUBLICATIONS

Office action dated Jul. 1, 2016 for TW application No. 104119817, filing date: Jun. 18, 2015, p. 1 line 1~14, pp. 2~3 and p. 4 line 1~9.
Office action dated Apr. 21, 2016 for the Taiwan application No. 104119817, filing date: Jun. 18, 2015 p. 1 line 1~14, p. 2~4 and p. 5 line 1~23.

* cited by examiner

*Primary Examiner* — Kerri L McNally
(74) *Attorney, Agent, or Firm* — Winston Hsu

(57) ABSTRACT

A radio frequency module coupled to an object is disclosed. The radio frequency module includes an antenna unit, operating in one of a first mode and a second mode to receive a radio frequency signal and to transmit an identification signal, wherein the frequencies of the radio frequency signal and the identification signal is an operation frequency; and a chip unit, coupled to the antenna unit and is utilized for generating the identification signal according to the radio frequency signal received by the antenna unit.

14 Claims, 5 Drawing Sheets

RADIO FREQUENCY MODULE AND RELATED MANAGEMENT SYSTEM

BACKGROUND OF THE INVENTION

1. Field of the Invention

The present invention relates to a radio frequency module and related management system, and more particularly, to a radio frequency module applied to the warehouse management and/or the drug dosage monitoring system and related management system.

2. Description of the Prior Art

Generally, the conventional drip monitoring method and related drip monitoring system realize the function of monitoring the drip by sensors and measurement circuits. However, the costs of the conventional drip monitoring method and related drip monitoring system are relative high and the performance of the conventional drip monitoring method and related drip monitoring system is unsatisfactory. For example, the conventional drip monitoring method and related drip monitoring system need to set a reader on the drip stand, to shorten the distance between the reader and a monitoring module on the drip bag. Next, the conventional art connects the reader to a computing device in a wired manner and the computing device transmits the monitoring result to the corresponding computer or management system in a wireless manner. In other words, the conventional drip monitoring system needs at least 3 pairs of transmitting modules. The manufacture cost of the drip monitoring system is therefore increased. Thus, how to reduce the manufacture cost of the drip monitoring system becomes a topic to be discussed.

SUMMARY OF THE INVENTION

In order to solve the above problem, the present invention provides a radio frequency module applied to the warehouse management and/or the drug dosage monitoring system and related management system.

The present invention discloses a radio frequency module coupled to an object, the radio frequency module comprises an antenna unit, operating in one of a first mode and a second mode, to receive a radio frequency signal and to transmit an identification signal, wherein the frequencies of the radio frequency signal and the identification signal is an operation frequency; and a chip unit, coupled to the antenna unit and is utilized for generating the identification signal according to the radio frequency signal received by the antenna unit.

The present invention further discloses a management system. The management system comprises a reading module, for transmitting a radio frequency signal and receiving an identification signal, wherein the frequencies of the radio frequency signal and the identification signal is an operation frequency; and a radio frequency module coupled to an object. The radio frequency module comprises an antenna unit, operating in one of a first mode and a second mode, to receive a radio frequency signal and to transmit an identification signal, wherein the frequencies of the radio frequency signal and the identification signal is an operation frequency; and a chip unit, coupled to the antenna unit and is utilized for generating the identification signal according to the radio frequency signal received by the antenna unit.

These and other objectives of the present invention will no doubt become obvious to those of ordinary skill in the art after reading the following detailed description of the preferred embodiment that is illustrated in the various figures and drawings.

DETAILED DESCRIPTION

Figure 1:
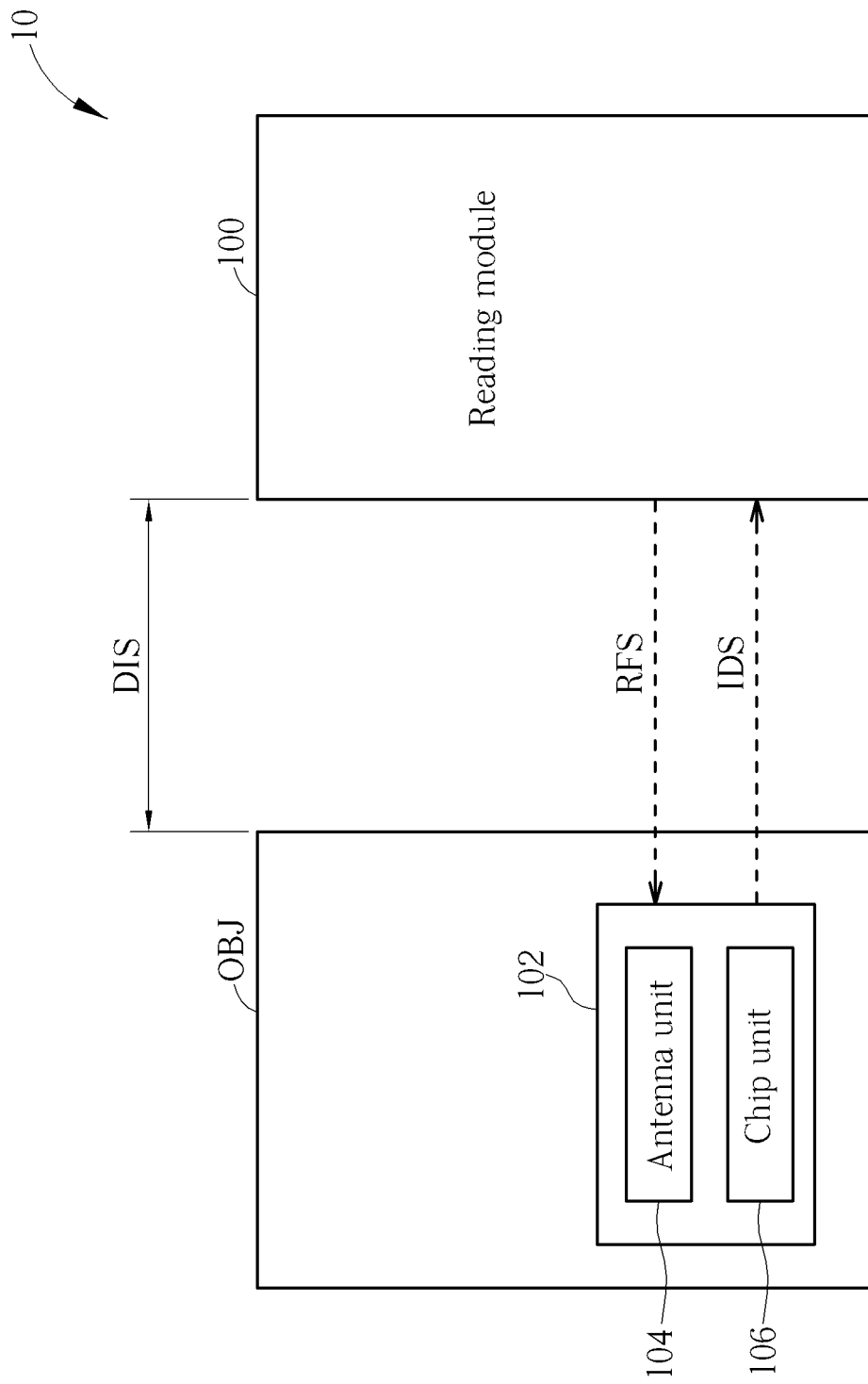
FIG. 1 is a schematic diagram of a management system according to an example of the present invention.

Please refer to FIG. 1, which is a schematic diagram of a management system 10 according to an example of the present invention. The management system 10 may be a warehouse management system or a drug dosage monitoring system, and is not limited herein. As shown in FIG. 1, the management system 10 comprises a reading module 100 and a radio frequency module 102. The reading module 100 may be a reader and is utilized for transmitting a radio frequency signal RFS whose frequency is an operation frequency FO. The radio frequency module 102 may be a radio frequency identification (RFID) Tag and is coupled (e.g. attached) to an object OBJ. The radio frequency module 102 comprises an antenna unit 104 and a chip unit 106 and is utilized for receiving the radio frequency signal RFS and generates an identification signal IDS. According to a relative permittivity (i.e. dielectric constant) of the object OBJ, the antenna unit 104 operates in one of modes MOD1 and MOD2 to receive the radio frequency signal RFS and to transmit the identification signal IDS. The frequencies of both the radio frequency signal RFS and the identification signal IDS are the operation frequency FO and the mode MOD2 is a harmonic mode of the mode MOD1. That is, the radio frequency module 102 switches the operation mode to transmit the identification signal IDS when the relative permittivity of the object OBJ changes, so as to allow the reading module 100 to perform subsequent operations according to the identification signal IDS.

Figure 2:
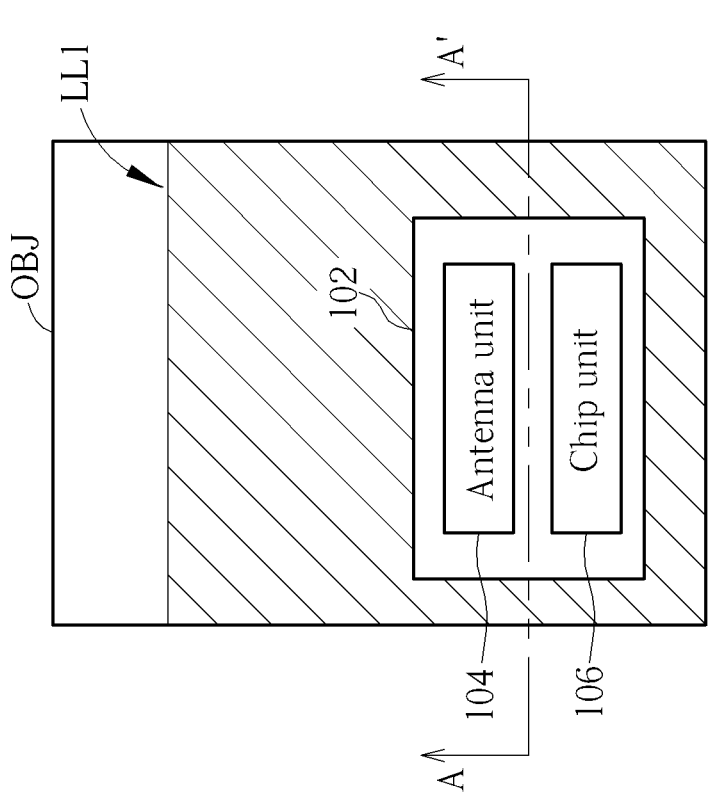
FIG. 2 is a schematic diagram of an example of the object and the radio frequency module shown in FIG. 1.

In details, the object OBJ is a container filled with liquid (e.g. a drip bag filled with glucose solution or physiological saline). Please refer to FIG. 2, which is a schematic diagram of an example of the object OBJ and the radio frequency module 102 shown in FIG. 1. In FIG. 2, the object OBJ contains great amount of liquid LIQ (e.g. an unused drip bag) and the liquid level of the liquid LIQ is a liquid level LL1. In this example, the radio frequency module 102 is configured on a substrate SUB and the substrate SUB is coupled (e.g. attached) to a bag body layer of the object OBJ. For example, the substrate SUB is composed of Fiber-reinforced plastic and the bag body layer BB is composed of Polyvinylchloride (PVC). Since the radio frequency module 102 is coupled to the object OBJ via the substrate SUB, the operations of the radio frequency module 102 is affected by the relative permittivity of the object OBJ. In the example, the relative permittivity of the object OBJ approximates a relative permittivity DC1 of the liquid LIQ and the antenna unit 104 operates in the mode MOD2 when the relative permittivity of the object OBJ approximates the relative permittivity DC1. The working frequency of the antenna unit 104 operating in the mode MOD2 is design at the operation frequency FO of the radio frequency signal FO. Under such a condition, the antenna unit 104 receives the radio frequency signal RFS and transmits the identification signal IDS that is generated by the chip unit 106 according to the radio frequency signal RFS.

Figure 3:
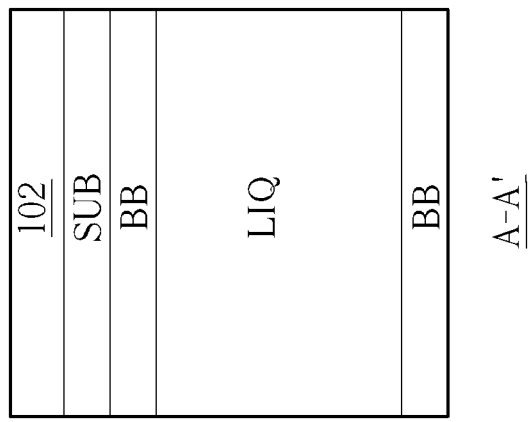
FIG. 3 is another example of the object and the radio frequency module shown in FIG. 1.
Figure 3:
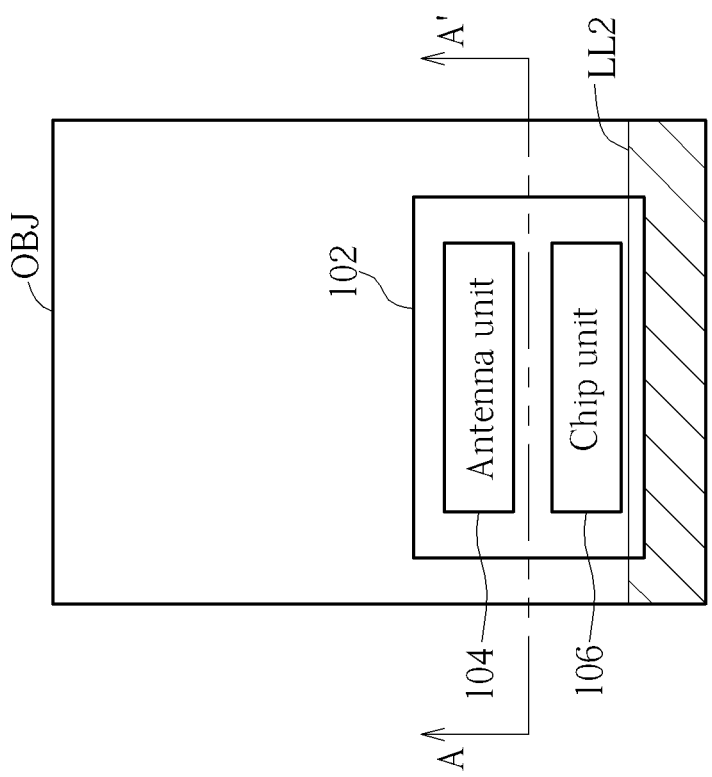

Please refer to FIG. 3, which is a schematic diagram of another example of the object OBJ and the radio frequency module 102. In comparison with FIG. 2, the liquid level of the liquid LIQ in the object is decreased from the liquid level LL1 to the liquid level LL2 (e.g. a used drip bag). The relative permittivity of the object OBJ changes to approximate a relative permittivity DC2 of the air. The relative permittivity DC1 of the liquid LIQ is much greater than the relative permittivity DC2 of the air and the antenna unit 104 operates in the mode MOD1 when the relative permittivity of the object OBJ approximates the relative permittivity DC2. The working frequency of the antenna unit 104 operating in the mode MOD1 is also designed at the operation frequency FO of the radio frequency signal RFS. Even if the relative permittivity of the object OBJ changes because the liquid LIQ in the object OBJ is consumed, the antenna unit 104 still can receive the radio frequency signal RFS and transmit the identification signal IDS, which is generated by the chip unit 106 according to the radio frequency signal RFS.

Figure 4:
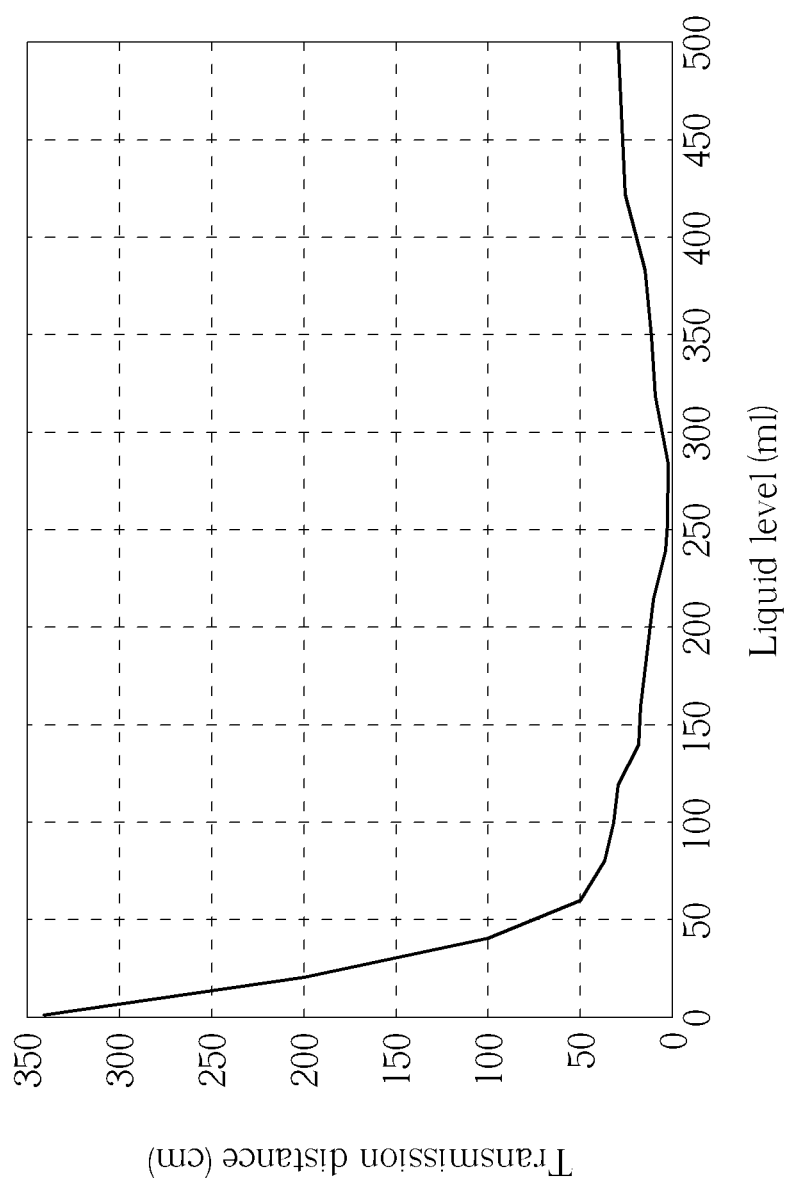
FIG. 4 is a schematic diagram of the relationship between the transmission distance of the identification signal and the liquid level height in the object.

According to the above, the antenna unit 104 is switched from the mode MOD2 to MOD1 when the liquid level of the liquid LIQ in the object OBJ decreases from the liquid level LL1 to LL2, to receive the radio frequency RFS and to transmit the identification signal IDS at the same operation frequency FO. Note that, the transmission distance of the identification signal IDS transmitted by the antenna unit 104 operating in mode MOD2 is smaller than that of the identification signal IDS transmitted by the antenna unit 104 operating in the mode MOD1 because the relative permittivity DC1 of the liquid LIQ is greater than the relative permittivity DC2 of the air. Please refer to FIG. 4, which is a schematic diagram of relationships between the transmission distance of the identification signal IDS and the liquid level of the liquid LIQ in the object OBJ. In FIG. 4, the liquid level of the liquid LIQ in the object OBJ is represented by the volume of the liquid LIQ in the object OBJ. As shown in FIG. 4, the transmission distance of the identification signal IDS is smaller than 50 centimeter (cm) when the volume of the liquid LIQ in the object is greater than 60 milliliter (ml). After the volume of the liquid LIQ in the object OBJ becomes smaller than 60 ml, the transmission distance of the identification signal IDS significantly increases.

According to the difference between the transmission distances of the identification signals IDS generated by the antenna unit 104 operating in different modes, the management system 10 can realize different applications via altering the distance between the reading module 100 and the object OBJ. In an example, the management system 10 is a warehouse management system of the object OBJ. In this example, a distance DIS between the reading module 100 and the object OBJ is designed to be smaller than a predefined distance PD1 (e.g. 20 cm). When the object OBJ is manufactured, the object OBJ is filled with the liquid LIQ (e.g. the object OBJ shown in FIG. 2) and the antenna unit 104 operates in the mode MOD2. The transmission distance of the identification signal IDS generated by the antenna unit 104 operating in the mode MOD2 is greater than the predefined distance PD1. Thus, the reading module 100 can receive the identification signal IDS when the object OBJ leaves the factory or enters the warehouse and record the inventory of the object OBJ.

In another example, the management system 10 is a consumption monitoring system of the object OBJ. In this example, the distance DIS between the reading module 100 and the object OBJ is designed to be a predefined distance PD2 (e.g. 2 meters). When the object OBJ just starts being used (e.g. the drip bag starts being used in the intravenous injection), the object fills with the liquid LIQ and the antenna unit 104 operates in the mode MOD2. Because the transmission distance of the identification signal IDS generated by the antenna unit 104 operating in the mode MOD2 is smaller than the predefined distance PD2, the reading module 100 cannot receive the identification signal IDS. The liquid level of the liquid LIQ in the object OBJ gradually decreases when the liquid LIQ in the object is continuously consumed. When the liquid level of the liquid LIQ decreases to an alert level, the antenna unit 104 switches to the mode MOD1 and the transmission distance of the identification signal IDS becomes greater than the predefined distance PD2. The reading module 100 starts receiving the identification signal IDS and acknowledges that the liquid level of the liquid LIQ in the object decreases to the alert level.

The radio frequency module 102 of the above examples operates in one of the modes MOD1 and MOD2, to receive the radio frequency signal RFS and to transmit the identification signal IDS even if the relative permittivity of the object OBJ changes from the relative permittivity DC1 to DC2. Via appropriately designing the distance between the reading module 100 and the object OBJ attached by the radio frequency module 102, the management system 10 can be applied to different applications. According to different applications and design concepts, those with ordinary skill in the art may observe appropriate alternations and modifications. For example, the radio frequency module 102 may directly couple to the object OBJ. In other words, the substrate SUB shown in FIGS. 2 and 3 can be omitted. The manufacture cost of the management system 10 is therefore reduced.

Figure 5:
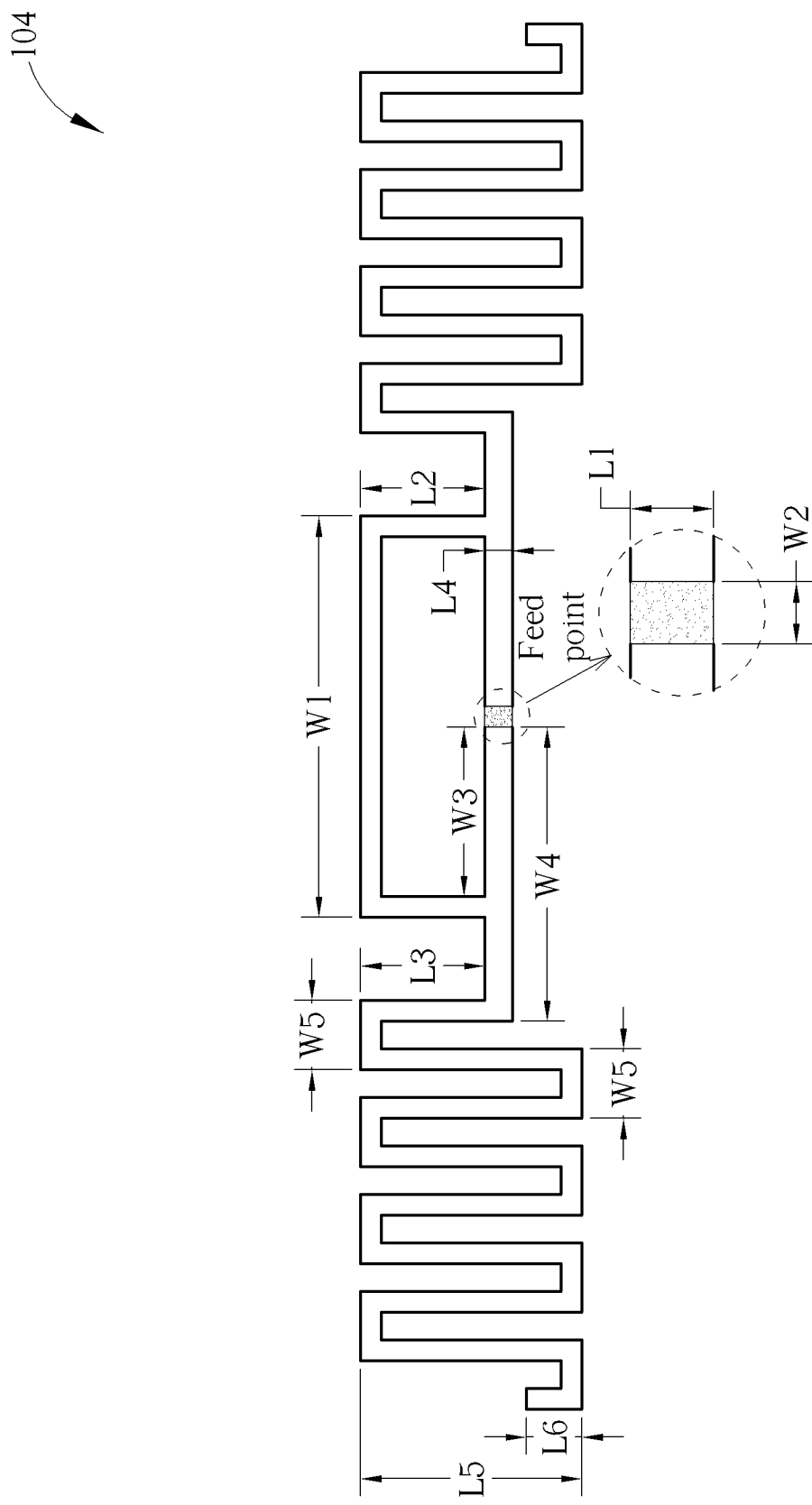
FIG. 5 is a schematic diagram of the antenna unit shown in FIG. 1.

Please refer to FIG. 5, which is a schematic diagram of the antenna unit 104 shown in FIG. 1. In FIG. 5, the antenna unit 104 equips with symmetric structure. In an example, the lengths L1-L6 of the antenna unit 104 shown in FIG. 5 are 5.8 millimeters (mm), 6 mm, 6.2 mm, 1.8 mm, 12 mm, and 3 mm, respectively. The widths W1-W5 of the antenna unit 104 shown in FIG. 5 are 23 mm, 1 mm, 7 mm, 13 mm, and 3 mm, respectively. According to different applications and design concepts, the antenna unit 104 may be realized in various structures and/or sizes, and is not limited to the structure and size shown in FIG. 5.

To sum up, the radio frequency module switches the operation mode when the relative permittivity of the object coupled to the radio frequency module changes, to contiguously transmit the identification signal. Further, the management system of the above examples can be applied to different applications via appropriately designing the distance between the reading module and the object coupled to the radio frequency module. For example, the radio frequency module and related management system of an example of the present invention can be applied to the warehouse management and the drug dosage monitoring, to reduce additional manufacture cost.

Those skilled in the art will readily observe that numerous modifications and alterations of the device and method may be made while retaining the teachings of the invention.

Accordingly, the above disclosure should be construed as limited only by the metes and bounds of the appended claims.

What is claimed is:

1. A radio frequency module coupled to an object, the radio frequency module comprising:
   an antenna unit, operating in one of a first mode and a second mode to receive a radio frequency signal and to transmit an identification signal, wherein the frequencies of the radio frequency signal and the identification signal is an operation frequency; and
   a chip unit, coupled to the antenna unit and is utilized for generating the identification signal according to the radio frequency signal received by the antenna unit;
   wherein the object is a drip bag.

2. The radio frequency module of claim 1, wherein a first distance of the identification signal transmitted by the antenna unit operating in the second mode is smaller than a second distance of the identification signal transmitted by the antenna unit operating in the first mode.

3. The radio frequency module of claim 1, wherein the object is a container filled with liquid.

4. The radio frequency module of claim 1, wherein the antenna unit operates in the first mode when the relative permittivity of the object is a first relative permittivity and the antenna unit operates in the second mode when the relative permittivity of the object is a second relative permittivity, wherein the second relative permittivity is greater than the first relative permittivity.

5. The radio frequency module of claim 1, wherein the radio frequency module is attached to the object.

6. The radio frequency module of claim 1, the radio frequency module is configured on a substrate and the substrate is attached to the object.

7. A management system, comprising:
   a reading module, for transmitting a radio frequency signal and receiving an identification signal, wherein the frequencies of the radio frequency signal and the identification signal is an operation frequency; and
   a radio frequency module coupled to an object, the radio frequency module comprising:
      an antenna unit, operating in one of a first mode and a second mode, to receive a radio frequency signal and to transmit an identification signal, wherein the frequencies of the radio frequency signal and the identification signal is an operation frequency; and
      a chip unit, coupled to the antenna unit and is utilized for generating the identification signal according to the radio frequency signal received by the antenna unit;
   wherein the object is a drip bag.

8. The management system of claim 7, wherein a first distance of the identification signal transmitted by the antenna unit operating in the second mode is smaller than a second distance of the identification signal transmitted by the antenna unit operating in the first mode.

9. The management system of claim 7, wherein the object is a container filled with liquid.

10. The management system of claim 7, wherein the antenna unit operates in the first mode when the relative permittivity of the object is a first relative permittivity and the antenna unit operates in the second mode when the relative permittivity of the object is a second relative permittivity, wherein the second relative permittivity is greater than the first relative permittivity.

11. The management system of claim 10, wherein the distance between the reading module and the radio frequency module is greater than a predefined distance and the reading module receives the identification signal transmitted by the antenna unit operating in the first mode.

12. The management system of claim 10, wherein the distance between the reading module and the radio frequency module is smaller than a predefined distance and the reading module receives the identification signal transmitted by the antenna unit operating in the second mode.

13. The management system of claim 7, wherein the radio frequency module is attached to the object.

14. The management system of claim 7, the radio frequency module is configured on a substrate and the substrate is attached to the object.

* * * * *